United States Patent
Bergad (10) Patent No.: US 11,026,856 B1
(45) Date of Patent: Jun. 8, 2021

(54) SURGICAL UNDERLAY PAD FOR SECURING A PATIENT TO AN OPERATING TABLE IN A TRENDELENBURG POSITION

(71) Applicant: Bergad, Inc., Kittanning, PA (US)

(72) Inventor: Paul Bergad, Freeport, PA (US)

(73) Assignee: Bergad, Incorporated, Kittanning, PA (US)

(*) Notice: Subject to any disclaimer, the term of this patent is extended or adjusted under 35 U.S.C. 154(b) by 206 days.

(21) Appl. No.: 16/122,209

(22) Filed: Sep. 5, 2018

(51) Int. Cl.
*A61G 13/12* (2006.01)
*A61B 5/00* (2006.01)
*A61G 13/00* (2006.01)
*A61G 7/10* (2006.01)

(52) U.S. Cl.
CPC .......... *A61G 13/127* (2013.01); *A61B 5/704* (2013.01); *A61G 7/10* (2013.01); *A61G 13/0036* (2013.01); *A61G 13/122* (2013.01); *A61G 13/1225* (2013.01)

(58) Field of Classification Search
CPC ........ A61G 1/06; A61G 13/12; A61G 13/127; A61G 13/0036; A61G 13/122; A61G 13/1225; A61G 13/123; A61G 13/126; A61G 7/10; A61G 7/065; A61G 7/07; A61B 5/704
See application file for complete search history.

(56) References Cited

U.S. PATENT DOCUMENTS

| 8,418,297 B2* | 4/2013 | Mikkelsen | A47G 9/10 |
|---|---|---|---|
| | | | 5/740 |
| 8,464,270 B2 | 6/2013 | Pigazzi et al. | |
| 8,511,314 B2* | 8/2013 | Pigazzi | A61G 13/10 |
| 9,161,876 B2* | 10/2015 | Pigazzi | A61F 5/30 |
| 9,782,287 B2 | 10/2017 | Pigazzi et al. | |
| 2007/0246157 A1* | 10/2007 | Mason | A47C 27/085 |
| | | | 156/242 |
| 2009/0276957 A1* | 11/2009 | Boitet-Ball | A47G 27/0237 |
| | | | 5/420 |
| 2012/0244312 A1* | 9/2012 | Pearce | D06N 7/0092 |
| | | | 428/136 |
| 2012/0260421 A1* | 10/2012 | DeGregorio | A47G 27/0206 |
| | | | 5/417 |
| 2017/0189255 A1* | 7/2017 | Holladay | A61G 13/121 |
| 2017/0231849 A1* | 8/2017 | Holladay | A61G 13/126 |
| | | | 5/620 |
| 2017/0239118 A1* | 8/2017 | Cole | A61G 13/102 |

OTHER PUBLICATIONS http://www.xodusmedical.com/PinkPadVideo video showing features of an underlay pad described in various Pigazzi patents.

* cited by examiner

*Primary Examiner* — Robert G Santos
*Assistant Examiner* — Rahib T Zaman
(74) *Attorney, Agent, or Firm* — Karen Tang-Wait Sutton (57) ABSTRACT

A surgical underlay pad to secure a patient's torso while in a Trendelenburg position, the pad comprised of a flexible substrate with an adhesive gel coat on one or more sides of the substrate having a shear strength such that when the pad is positioned on an operating table surface and the table is tilted, the pad and the torso positioned on the pad resist sliding. The gel coat can be applied as a continuous coating or in a variety of patterns. The pad is removable and the gel coat forms a water resistant bond with the operating table surface. The gel coat reduces the overall mass of the pad, and is cost effective, easier to manufacture, and produces less environmental waste.

13 Claims, 6 Drawing Sheets

| | |
|---|---|
| Firmness of foam substrate in lbs (measured at 25% IFD) | <5 to 350 |
| Gel layer composition | One of or mix of flexible polymeric carrier solvated PCBTF, hydrocarbon solvents, aliphatic hydrocarbon solvents, polar solvents AND compounded with at least one or more performance enhancing additive |
| Gel layer adhesion characteristics | Gel layer must be able to adhere the gel pad to the operating table such that the table can be tilted beyond or below a horizontal position and the gel pad will maintain its original position on the operating table |
| Substrate Coating method | Rolling, spraying, pouring |

SURGICAL UNDERLAY PAD FOR SECURING A PATIENT TO AN OPERATING TABLE IN A TRENDELENBURG POSITION

CROSS REFERENCE TO RELATED APPLICATIONS

NA

STATEMENT REGARDING FEDERALLY SPONSORED RESEARCH OR DEVELOPMENT

NA

NAMES OF THE PARTIES TO A JOINT RESEARCH AGREEMENT

NA

INCORPORATION BY REFERENCE OF MATERIAL SUBMITTED ON A COMPACT DISC OR AS A TEXT FILE VIA THE EFS WEB SYSTEM

NA

STATEMENT REGARDING PRIOR DISCLOSURES BY THE INVENTOR OR A JOINT INVENTOR

NA

BACKGROUND OF THE INVENTION

A Trendelenburg position refers to a position during a medical operation where a patient's body on an operating table is tilted, with a patient's head lower than the legs, and with a reverse Trendelenburg position being one in which the patient's head is higher than the legs. In this disclosure, "Trendelenburg position" is used to describe both situations and covers any angle of the operating table other than the table being horizontal or parallel with a floor surface. Commonly used for abdominal and genitourinary surgeries, the Trendelenburg position often must be maintained for extended periods of time, and this presents multiple challenges: safely maintaining the position during the entire operation time, effective use of pre-surgical preparation time securing the patient to the operating table; and ease of positioning of the patient prior to, during, and post-surgery.

In the prior art, there are several patents for a widely used pad known as the Pink Pad®, U.S. Pat. Nos. 8,464,720, 8,511,314, 9,161,876, 9,750,656, and 9,782,287 (hereinafter collectively referred to as "the Pigazzi patents"). The Pigazzi patents describe a method and system for securing a patient to an operating table in the Trendelenburg position, part of which involves the use of a viscoelastic foam pad positioned between the operating table and a sheet that covers at least some of the upper surface are of the pad, with the patient positioned on top of the sheet and whose body partially rests directly on the pad. The pad itself is secured to the operating table via hook and loop closures, and the patient is then further secured to the table and pad via body straps. The viscoelastic pad described in the Pigazzi patents is described as being able to reduce pressure points of the body lying on it and thus minimizing patient discomfort, prevention of body sores due to pressure, maintain body temperature, and also maintain the Trendelenburg position by the pad's ability to "hold" the patient's body securely on the operating table, the overall holding capabilities of the system being a combination of the pad, body straps, and co-efficient of friction with respect to the patient and the table, the pad and the sheet, and the sheet and the patient.

While the system described in the Pigazzi patents works reasonably well, the Pigazzi system is highly dependent on the physical characteristics of the pad, specifically the ability of the pad to effectively grip the table and the patient's body. Importantly, some of the physical characteristics of the viscoelastic foam, commonly called memory foam, used in the Pigazzi patents have serious drawbacks in current surgical applications. Viscoelastic foams are relatively expensive to produce compared to other polyurethane foams due to more complicated manufacturing processes, and thus this is an important consideration for a disposable product that is designed to be single use only due to hygienic concerns. Another inherent problem with viscoelastic foam used as a surgical underlay pad is that these foams become slippery and are more easily torn when wet, and thus can lose its gripping properties when exposed to moderate to excessive amounts of fluids, either bodily or solutions, during surgery. Finally, as viscoelastic foams are temperature sensitive, the foam becomes softer as it warms up, and thus can lose its support properties when warmed, requiring careful temperature control and monitoring thereof.

What is needed is an improved disposable surgical underlay pad for securing the patient in the Trendelenburg position, the pad featuring improved gripping qualities as well as being cost effective when compared to the prior art viscoelastic pads.

FIELD OF THE INVENTION

The present invention pertains to the field of polyurethane based gels, thermally conductive materials, and phase change materials, specifically, to surgical underlay pads at least partially comprised of polyurethane gels used during surgery when a Trendelenburg position is required.

BRIEF SUMMARY OF THE INVENTION

A surgical underlay pad for securing a torso of a patient to an operating table that is tilted beyond a horizontal position during a surgical operation, the pad having a flexible substrate coated on at least one of an under side and an upper side with a polyurethane gel material so as to form a gel coat. The gel coat has sufficient shear strength so as to prevent the surgical underlay pad from slipping when the operating table is tilted beyond a horizontal plane, and when the substrate is coated on both the upper and lower sides, the gel coat additionally prevents a torso of the patient supported on the surgical underlay pad from sliding across the pad. The flexible substrate is comprised of an open cell polyurethane foam, a paper material, fabric, and combinations thereof.

In yet another embodiment, the surgical underlay pad is a sheet of silicone sized and shaped to support the torso of a patient, the silicone having a low tack physical characteristic with a shear strength sufficient to prevent the surgical underlay pad from sliding across the operating table when the operating table is tilted beyond a horizontal position.

In still yet another embodiment, the gel coat is arranged in a predetermined pattern and thickness that can vary between the upper side and the lower side of the substrate.

BRIEF DESCRIPTION OF THE DRAWINGS

The features and advantages of the invention will become apparent from a consideration of the subsequent detailed description presented in connection with accompanying drawings, in which.

DRAWINGS LIST OF REFERENCE NUMERALS

The following is a list of reference labels used in the drawings to label components of different embodiments of the invention, and the names of the indicated components.
100 surgical underlay pad or gel pad
10 substrate
10a upper (patient) side of substrate
10b lower (table) side of substrate
20 gel coat or gel coating
20a dot pattern
20b stripe pattern
20c target pattern
22 gel pad
30 operating table
30a top surface of operating table
30b base of table
30c articulated leg portion of table
30d ground or floor surface
40 patient torso
40a patient head
40b patient leg
50 sheet

DETAILED DESCRIPTION

A surgical underlay pad, or gel pad 100 according to the invention is shown in the FIGS. 1-6.

Figure 1:
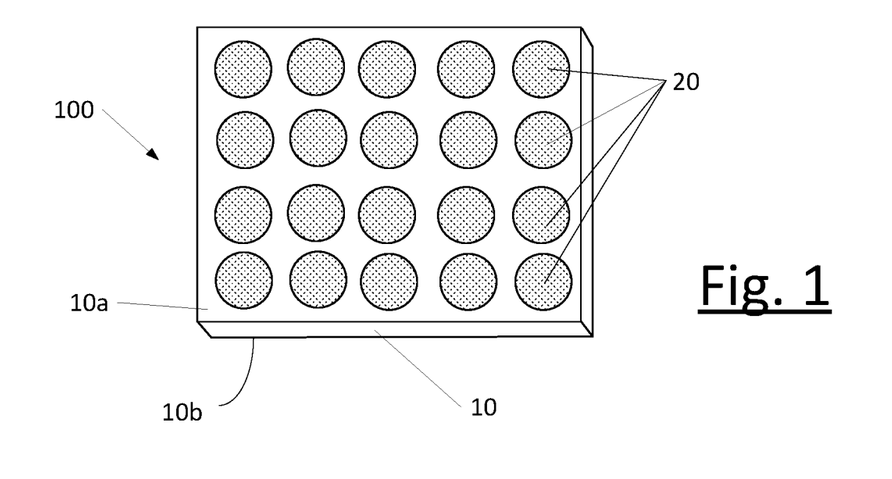
FIG. 1 is a perspective view of a first embodiment of an improved surgical underlay pad according to the invention, shown with an outermost gel layer adhered to or infused onto a substrate, shown in a first pattern.
Figure 2:
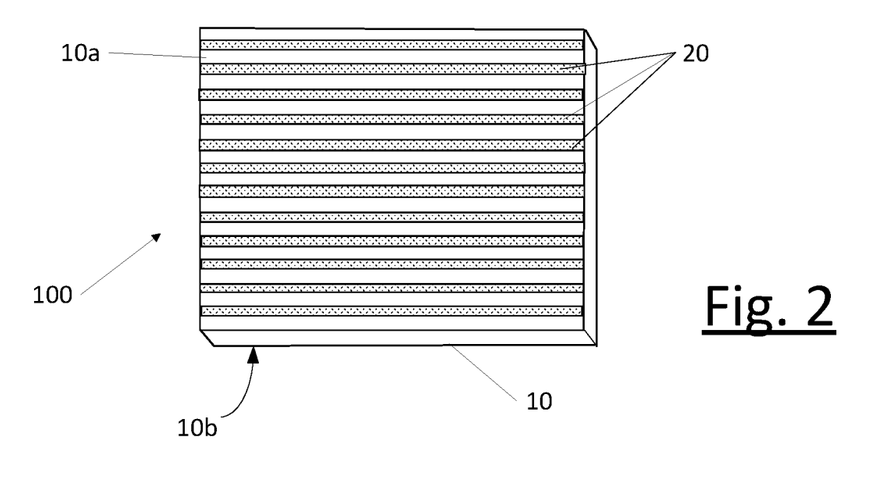
FIG. 2 is a second embodiment of an improved surgical underlay pad according to the invention, shown with an outermost gel layer adhered to or infused onto a substrate, where the gel layer is shown in a second pattern.
Figure 3:
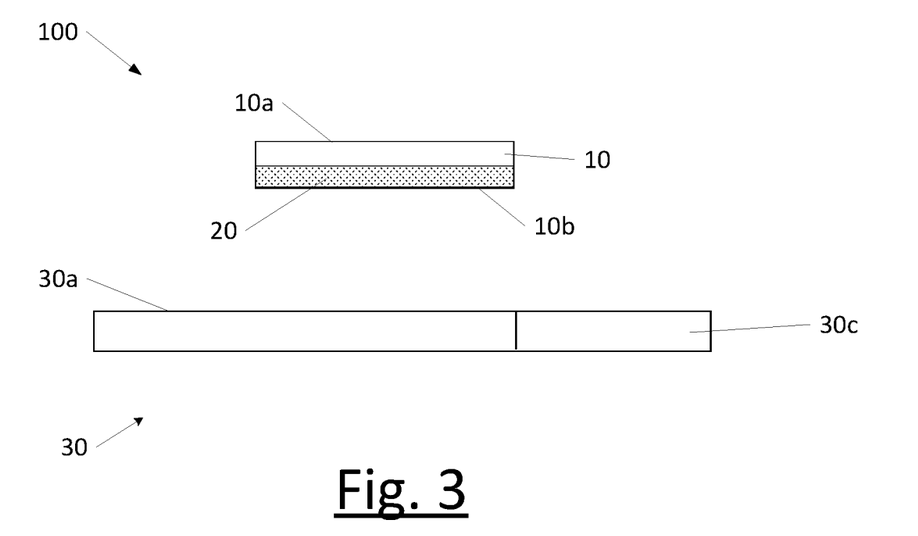
FIG. 3 is a side elevation view of the improved surgical underlay pad according to the invention, shown with an outermost gel layer adhered to or infused onto a bottom side of the substrate and shown in a exploded view with a surgical table top to show position and relative size of the pad.
Figure 4:
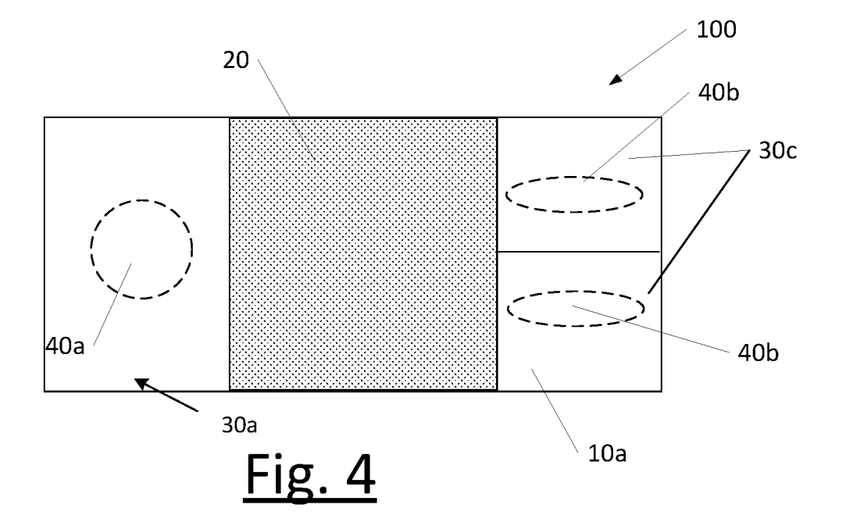
FIG. 4 is a top view of the improved surgical underlay pad according to the invention, shown in a third embodiment where the entire top surface of the substrate is shown with an outermost gel layer adhered to or infused to it, and showing approximate locations of a patient's head and leg positions relative to the pad.
Figure 6:
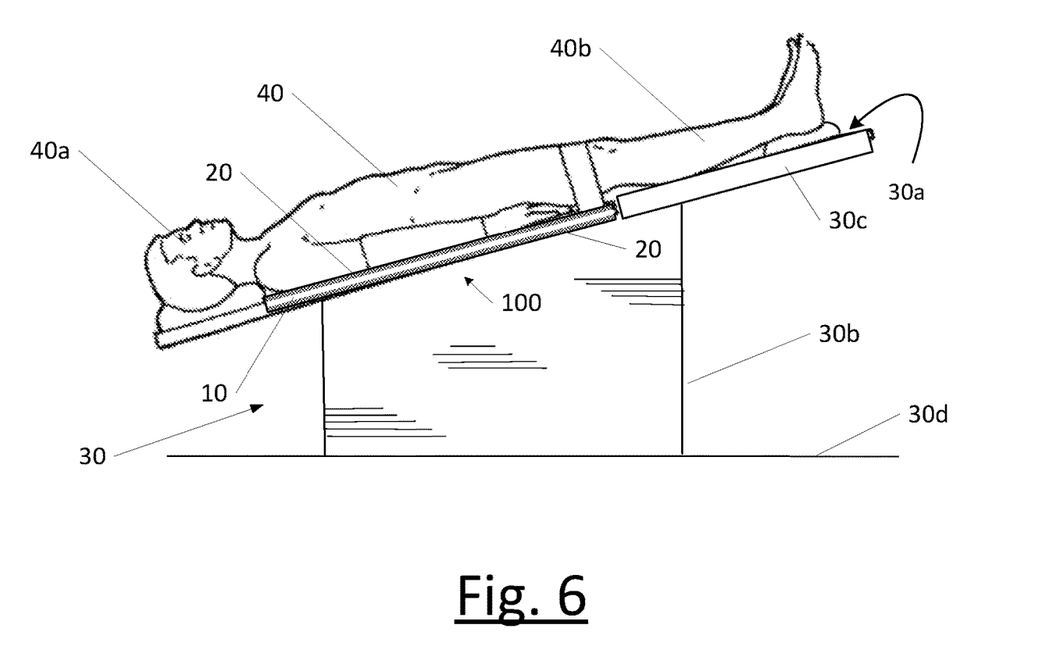
FIG. 6 is a side elevation view of a patient's body lying on the improved surgical underlay pad according to the invention, with the pad positioned on a surgical table in a Trendelenburg position.

Turning to the Figures, the gel pad 100 is comprised of a substrate 10 to which a gel coat 20 is applied. The gel coat 20 is applied to at least one of an upper side 10a and a lower side 10b of the substrate 10, typically to both upper 10a and lower sides 10b, as shown specifically in FIG. 6, or alternatively to only the lower side 10b of the substrate 10, as shown in FIG. 3 as desired. The gel coat 20 can be a uniform or continuous coating from edge to edge of the substrate's upper and/or lower side, and shown in FIG. 4, or be applied in a pattern, for instance, as a company logo, or as a repeating series of dots, stripes, or other patterns and shapes, as shown in the Figures. The inventor notes that while the Figures show a thickness of the gel coat on upper and lower sides to be approximately a same thickness, the thickness of the gel coat can vary between the upper and lower sides of the substrate, and patterns of gel coat on upper and lower sides of the substrate can also vary, so the patterns and relative thickness of the gel coat in the Figures are illustrative only of some possible patterns and are not meant to limit the thickness and pattern of the gel coat 20. FIGS. 4 and 6 show relative positioning of a patient's torso 40, head 40a and legs 40b on the surgical table top surface 30a and relative to the gel pad 100, with the patient's torso 40 lying on the gel pad 100 so as to be supported by the pad. The inventor notes that processes used to apply the gel coat include laminating as well as gel infusion processes. On the upper side of the substrate, the gel coat 20 can be selectively applied to areas to help center and position the patient on the pad, for instance, by creating more different surface patterns on the upper side of the substrate to indicate position of the patient's shoulders, etc. on the pad to allow optimal placement. The gel pad 100 is made in many sizes; however the main determination of size is that it be large enough to support the patient's torso 40 and is typically not so large as to be positioned under the patient's head 40a or legs 40b.

Figure 7:
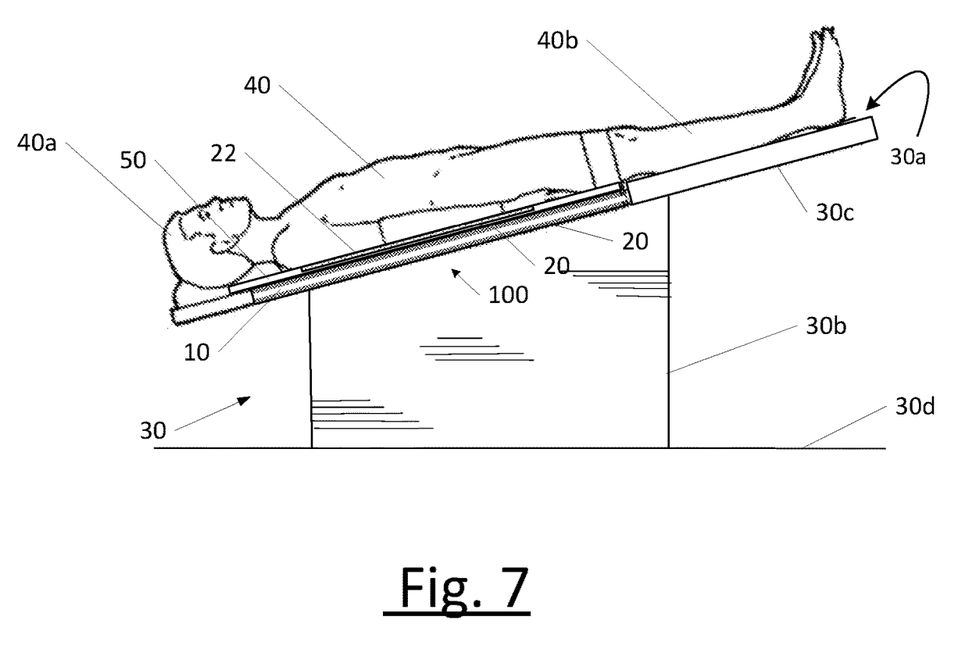
FIG. 7 is a side elevation view of the improved surgical underlay pad according to the invention, shown in a use position on a surgical table in a Trendelenburg position, and with a sheet having a gel pad configured to support a patient's torso positioned between the patient's torso and the improved surgical underlay pad.
Figure 8:
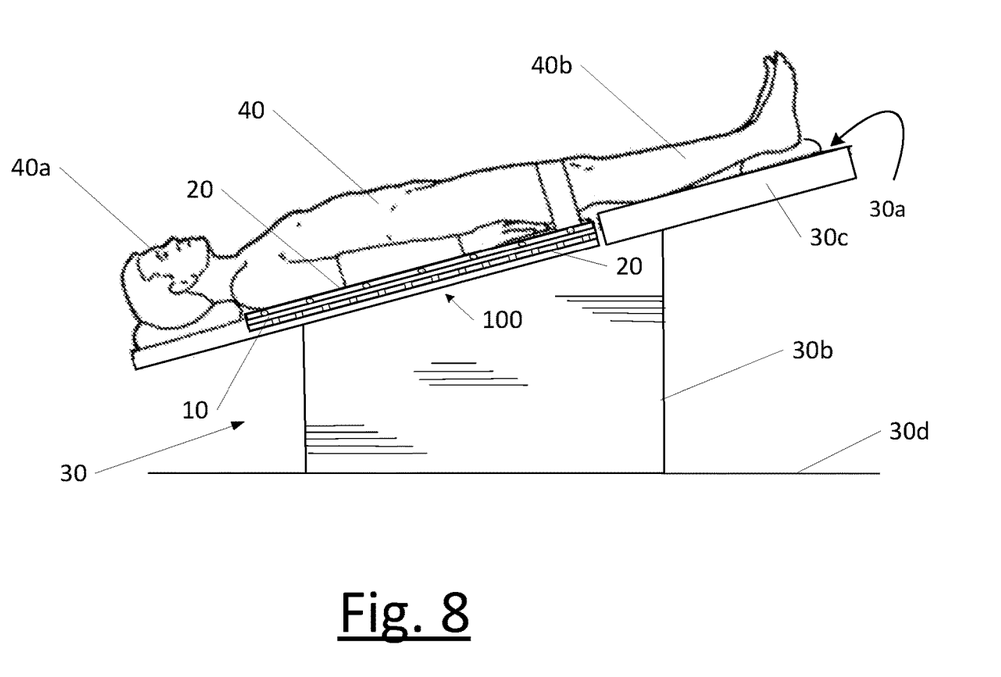
FIG. 8 is a side elevation view of the improved surgical underlay pad, shown with a first gel pattern on an upper or patient facing side of the substrate, and a second gel pattern on a lower or table facing side of the substrate.

Sheets 50 are often used underneath patients to allow easier transfer of the patient from hospital bed to operating table, and in one embodiment of the invention, a side of the sheet contacting the patient's body could be optimally coated with the gel pad 22 so as to safely stick to the patient's body, reducing body sliding and increasing the safety of the transfer from bed to table and back again. In lieu of a partially coated transfer sheet, a small disposable sheet with gel coat on both sides can be first placed on the main transfer sheet, with the patient then positioned on top of the gel coat prior to transferring the patient.

In cases where a different surgical underlay pad is used, the small disposable sheet having the gel coat on both sides can also be used between an underside of the surgical underlay pad and the top surface 30a of the operating table 30.

The substrate 10 can be any one of a number of suitable pad materials, including viscoelastic foam, but more generally flexible open cell polyurethane foams, plastics, woven cloth, paper, and combinations of cloth, paper and plastics, as well as laminations having two or more materials that have desirable features in a surgical underlay pad, such as absorbency and patient comfort, with the added benefit of reduced cost and excellent maintenance of the Trendelenburg position throughout a surgical procedure.

The use of non-viscoelastic foam substrates as described herein greatly decreases the cost of the gel pad 100, an important consideration for a single use, disposable pad, while providing superior grip that would eliminate a plurality of hook and loop closures that form a necessary part of the Pigazzi system to prevent the pad from slipping, as well as provide more pad options for a surgical team. The inventor notes too that the use of the outermost gel layer is compatible with the Pigazzi system and is an improvement over the existing Pigazzi system that currently uses viscoelastic without gel. The inventor's gel pad 100 can use environmentally friendly substrates that take up significantly less volume when disposed, and depending on the surgery performed, a less voluminous underlay pad that does not rise up around the patient's body may be more desirable in a specific surgical application as a pad lying flatter against the operating table provides for better air circulation, and better visibility to prevent items from being unwittingly lost or trapped between the patient's body and the pad rising up around the body. Leaking of fluids, from the patient's body or otherwise, is far more easily recognized if a paper substrate is used, as compared with the viscoelastic Pigazzi pad, which would readily absorb the liquid and not necessarily leave any visible trace of it. The paper substrate, however, would still absorb the liquid but it would be readily apparent that leaking was occurring.

The foam substrate can also optionally incorporate thermally conductive material (TCM) and/or phase change material (PCM), typically a phase change gel. Phase change gel is a gel polymer containing one or more phase change materials and used within a polyether polyurethane foams, polyester polyurethane flexible foams or latex foams and relate to foams so made, and more particularly relate to gel polymers containing one or more phase change materials in polyether or polyester polyurethane flexible foams or latex foams. TCM is comprised of a flexible cellular foam and a phase change material interspersed uniformly throughout the cellular foam, or alternatively laminated onto the cellular foam substrate. Use of TCM and/or PCM in the substrate can help maintain the patient's body temperature as these materials are known for their moisture and temperature controlling properties. The Pigazzi pad uses viscoelastic, commonly called memory foam, advertising the memory foam helps with temperature regulation, however memory foam in the mattress industry is well known for its ability to absorb and retain body heat to a point where the retained heat causes the body to become uncomfortably warm. Some people enjoy the warming properties of memory foam in mattresses, but during surgery, temperature regulation of the patient's body is important, and the Pigazzi pad tends to increase body heat rather than maintain it. The gel pad 100, in contrast, using TCM and/or PCM in the substrate, would be able to help the patient's body maintain a constant temperature as excessive heat generation would simply be dissipated.

Significantly, the inventor notes that the Pigazzi pad, more expensive to make, is also far more expensive to throw away after its single use, because the pad must have a minimum depth for sufficient "gripping" action of the viscoelastic foam; if the viscoelastic foam is too thin, it is unable to sufficiently conform around the patient's body, and coupled with the reduced gripping ability of the foam around the patient when the pad absorbs heat from the patient's body, as well as from atmospheric heat generated by the surgical staff, lighting and equipment in the operating room that may or may not be tightly controlled, the Pigazzi pad's ability to secure the patient and pad to the operating table is compromised, and thus the mass of the pad must be increased to counteract all those variables to maintain the patient's Trendelenburg position. While it is possible to maintain general air temperature in the operating room, micro-pockets of heat around the operating table are inevitable, as are spills of bodily fluids and solutions that when absorbed by the Pigazzi pad, negatively affect the pad's holding qualities. Hence, each Pigazzi pad must have a predetermined and specific mass and volume that is a significant disposal cost post-surgery. While viscoelastic foam can be recycled, the nature of a surgical use pad is such that incineration or landfill disposal is far more likely, with the relevant resulting environmental impacts of incinerating or burying large quantities of foam.

The gel coat 20 used in the gel pad 100 is a polyurethane-based gel having adhesive qualities, and as such, acting as an adhesive, having a shear strength sufficient to prevent sliding or slippage of the gel pad 100 when positioned on an operating table, and of the patient's body positioned on top of the gel pad 100 when the gel coat 20 is applied to the upper side of the substrate. The adhesive qualities prevent slippage but still allow the gel pad to be removed and repositioned, as desired, by starting at an edge of the gel pad and lifting the gel pad off the operating table to break the adhesive bond between table surface and gel coat, or by lifting and repositioning the patient's body on the gel coat 20, as desired. In the second example, the shear strength of the gel coat on the lower side of the gel pad must be sufficiently strong to resist the vertical force lifting the patient's body off the gel coat on the upper side of the substrate.

The term gel is used here to refer to a material with a substantially dilute, three dimensional cross-linked system, which exhibits no flow when in a steady-state. Gels can be soft and flexible, or hard and rigid, and for the present invention, the gel is soft and flexible. Mostly liquid by weight, gels nevertheless behave like solids due to the three-dimensional cross-linked network within the liquid. This crosslinking gives the gel its structure or hardness and contributes to its adhesive stick or tack. Gels are thus a dispersion of molecules of a liquid within a solid medium in which liquid particles are dispersed in the solid medium. In the foam industry, polyurethane foams are made by reacting polyols and diisocyanates, and a polyurethane gel is created by underreacting polyols and diisocyanates to create the cross-linked gel.

The inventor notes that a polyurethane gel is in effect a "failed" foam, as gel's tack is an undesirable characteristic, and thus this sort of foam is a throwaway product, an unwanted end result in the foam industry. It should be noted that in the prior art, a Pigazzi pad consists of viscoelastic foam, or more commonly, memory foam, and this type of foam is not inherently sticky or tacky. Viscoelastic foam is a type of open cell, flexible polyurethane foam and an alternative to conventional and HR (high resiliency) flexible polyurethane foams. Comfort is enhanced by the foam's ability to conform to the bodies shape and slow recovery feature. Its ability to "adhere" and "secure" to the operating table is a result of a combination of factors, including a patient's body weight, as well as hook and loop closures directly fixing the pad to an operating table, and to additional straps that secure the patient's body to the table itself. The Pigazzi pad, sitting on a surface of the operating table and held there by its own weight will eventually slide off the operating table when tilted past a certain angle because the viscoelastic has no adhesive qualities. Since the Pigazzi pad lacks inherent tack, the Pigazzi patents detail very specific characteristics of the pad to ensure that the pad will be able to "hold" the patient and overcome its negative qualities such as its ability to hold and conform to the patient's body dependent on temperature and the presence of liquid.

In contrast, the inventor's gel pad 100, using gel to coat the substrate, has inherent adhesive qualities and shear strength allowing it to grip the operating table and the patient's body lying on the gel pad, even without the use of straps and hook and loop closures as are specified by the Pigazzi patents as being necessary for their pad to "hold" the patient and prevent slipping during an operation using a Trendelenburg position.

Figure 5:
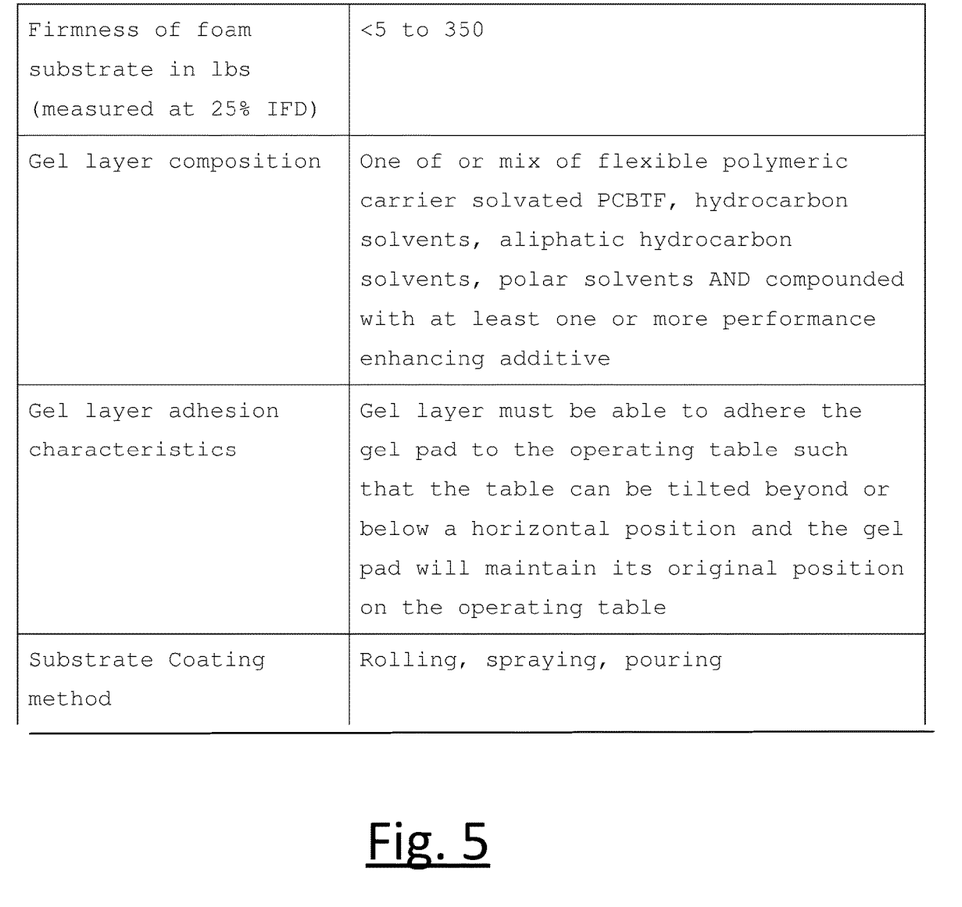
FIG. 5 is a table with a representative embodiment for the gel pad according to the invention featuring a viscoelastic foam substrate.

Turning to FIG. 5, a representative embodiment for the gel pad 100 according to the invention features a viscoelastic foam substrate having the following characteristics:

1. Firmness: range of less than 5 lbs. @ 25% IFD (soft) to 350 lbs. @ 25% IFD (semi-rigid). IFD means Indention Force Deflection, and is a measurable representation of how firm or soft the surface of a piece of foam feels. Also known as ILD (initial load deflection), IFD expresses comfort level as a number. Viscoelastic foam used for mattresses have IFD numbers usually ranging from 8 to 16.

2. Gel coat composition: The gel coat is a liquid gel mixture comprising at least one flexible polymeric carrier solvated parachlorobenzotrifluoride (PCBTF) or hydrocarbon solvents, aliphatic hydrocarbon solvents, polar solvents and mixtures of the aforementioned with the following characteristics:

A liquid gel mixture comprising at least one flexible polymeric carrier solvated parachlorobenzotrifluoride (PCBTF) or hydrocarbon solvents, aliphatic hydrocarbon solvents, polar solvents and mixtures of the aformentioned. The liquid gel mixture is formed by compounding the at least one flexible polymeric carrier, the PCBTF, and at least one performance-enhancing additive including plasticizers, solid fillers, phase change materials, thermally conductive materials, microencapsulated phase change materials, colorants, solvents, antioxidants, anti-static agents, anti-microbial agents, liquid flame retardants, solid flame retardants, ultraviolet stabilizers, surface tension modifiers, emulsifying agents, surfactants, fragrances, blowing catalysts, gelation catalysts, and combinations thereof.

3. Adhesion or Shear characteristics: The gel coat 20 is physically tacky to touch and has a shear strength sufficient to adhere the gel pad to the top surface 30a of the operating table 30 such that the gel pad 100 does not slip or otherwise change position on the table when the table is tilted in any direction above or below a horizontal position, and a patient lying on a gel coat also does not slip or slide across the gel coat when the table is tiled beyond the horizontal position. Note that the gel coat shear strength can vary between the upper and lower sides of the substrate, with the shear strength of the gel coat on the lower side, for instance, being relatively stronger than the shear strength of the gel coat on the upper side.

4. Substrate Coating Method: The gel coat can be applied by a roll coating system, spray coating, poured on the surface, or as an infusion where the substrate is impregnated with the gel.

The inventor notes that gel-infused foams exist in the prior art as a foam with gel embedded into the foam, and visco-gels being more recently known in the field of mattresses and bedding used to increase airflow through the foam and thus increase comfort by regulating the body temperature by avoiding heat buildup. The inventor, however, wishes to specifically point out that he is using gel as an adhesive, relying on the gel's physical tackiness and shear strength for his invention. Given that while embedding the gel within the viscoelastic foam itself in the surgical underlay pad increases the foam's tack, it also increases its density, manufacturing complexity and cost, and increased unnecessary durability for a single use, disposable product. Hence, the inventor believes that a surface treatment of gel is more cost effective that what is currently being used by the prior art Pigazzi pad.

The inventor wishes to point out that the gel coat 20 in his gel pad 100 is not an equivalent of a double sided tape or other removable adhesive known in the prior art. While the double sided tape might be used with a paper substrate to adhere the lower side of the substrate to the top surface of the operating table, tape can leave unwanted and potentially unsanitary residue on the top surface of the operating table 30a requiring special cleaning. Tape used on the patient's skin can leave unwanted adhesive residue as well, and is not easily repositionable or reusable. During surgery, it is not uncommon to position and reposition the patient, and a double sided paper tape, or plastic medical tape, for instance, used in lieu of the gel coat 20 would be impractical as its adhesive qualities deteriorate each time the patient is repositioned, and lacks sufficient strength to maintain the patient's position on the operating table when the table is tilted. Each time a patient is repositioned on the gel coat 20, the gel coat retains its ability to grip despite repositioning. Also, what if the substrate is fabric or foam? Securing the tape to the foam substrate is trickier because the foam is not a solid surface. Finally, as liquids such as blood and other solutions are commonly spilled onto surgical pads during surgery, the gel coat 20 has superior adhesive qualities as compared to a double sided tape; the gel coat 20 is highly liquid resistant and will not lose its strength when exposed to liquids. In comparison, tapes lose their adhesive strength when exposed to liquids. So long as the gel pad 100 is positioned onto a dry operating table surface, any spills of liquids will not compromise the gel pad's ability to grip the table and in embodiments where the gel coat is also on the upper side of the substrate, to continue to grip and hold the patient's torso 40 in position.

Latex is another common anti-slip material, but the inventor notes that many people are allergic to latex, and his gel pad 100 with its gel coat 20 is a less expensive and non-allergenic substitute for rubber that is safe against skin. It is also known that as viscoelastic foams can emit gases that may cause respiratory problems in certain individuals, a thin gel coat 20 on a non-foam substrate 10 as per the inventor's gel pad 100 is a fantastic alternative in cases where off-gassing is a concern to the patient or surgical team.

Finally, the inventor also notes in a particularly useful embodiment, a sheet of low tack silicone can also be used in lieu of the gel coat 20 and in some embodiments, to replace the substrate 10 itself. The inventor notes that depending on a thickness of the silicone layer used, the silicone could also provide cushioning as well as prevent the patient from sliding on the surgical table during a procedure in which a Trendelenburg position is required. Silicone has many similar properties in terms of adhesive qualities as compared to polyurethane gels, and the inventor thus wants to be clear that his invention can also be successful practiced using silicone layers adhered to the substrates 10 described herein, or combinations of gel and silicone, as desired.

The inventor notes that surgical teams are concerned about cost, but also about convenience. The gel pad 100 according to the invention can be incorporated into a kit that is sold along with disposable straps.

It is to be understood that the above-described arrangements are illustrative only of the application of the principles of the present invention, and that numerous modifications and alternative arrangements may be devised by those skilled in the art without departing from the scope of the present invention.

What is claimed is:

1. A surgical underlay pad (100) for securing a torso of a patient (40) to a top surface (30a) of an operating table (30), where the surgical underlay pad is positioned on the top surface and configured to support the torso prior to tilting the operating table beyond a horizontal position, the surgical underlay pad (100) comprising:
   a substrate (10) having an upper side (10a) and a lower side (10b); and
   a gel material forming a gel coat (20) affixed to at least a portion of the lower side of the substrate (10) and to the upper side of the substrate;
   wherein the substrate (10) is flexible and at least one of a polyurethane open cell foam, a paper based material, a fabric, and combinations thereof;
   wherein the gel coat (20) is a polyurethane gel having a shear strength;
   wherein the shear strength of the gel coat is of a sufficient strength to prevent the surgical underlay pad from sliding on the top surface after the operating table is tilted beyond the horizontal position;
   wherein the shear strength of the gel coat allows the surgical underlay pad to be repositioned by vertically lifting and repositioning the pad off the top surface of the operating table without affecting the shear strength of the gel coat;
   wherein the shear strength of the gel coat (20) applied to the lower side (10b) of the substrate has a first predetermined shear strength, and the sheer strength of the gel coat (20) applied to the upper side (10a) of the substrate has a second predetermined shear strength;
   wherein the gel coat on the upper side of the substrate is a predetermined pattern visually indicating a preferred positioning of the patient's body on the surgical underlay pad (100); and
   wherein the torso (40) is configured to be positioned on the gel coat (20) on the upper side of the substrate (10).

2. The surgical underlay pad (100) in claim 1, wherein the first predetermined shear strength and the second predetermined shear strength are a same shear strength.

3. The surgical underlay pad (100) in claim 1, wherein the first predetermined shear strength and the second predetermined shear strength are a different shear strength.

4. The surgical underlay pad (100) in claim 1, wherein the gel coat (20) is applied to the substrate (10) without adhesive.

5. The surgical underlay pad (100) in claim 1, wherein the gel coat (20) is an infusion of the gel material and the substrate.

6. The surgical underlay pad (100) in claim 1, wherein the substrate (10) is further comprised of at least one of a thermally conductive material and a phase change material.

7. The surgical underlay pad (100) in claim 1, wherein the substrate (10) is a viscoelastic foam.

8. The surgical underlay pad (100) in claim 1, wherein the gel coat (20) is a continuous coating on the lower side (10a) of the substrate (10).

9. The surgical underlay pad (100) in claim 1, wherein the gel coat (20) is applied in a predetermined pattern on the substrate.

10. A gel pad (100) for use with a surgical underlay pad supporting a torso (40) of a patient lying on a top surface (30a) of an operating table (30) tilted beyond a horizontal plane, the gel pad comprising:
    a flexible substrate (10) having an upper side (10a) and a lower side (10b); and
    a gel coat (20) comprising a polyurethane gel material on at least a portion of each of the lower side (10b) and the upper side (10a) of the substrate (10);
    wherein the gel coat on the upper side of the substrate is applied in a first predetermined pattern;
    wherein the gel coat on the lower side of the substrate is applied in a second predetermined pattern different from the pattern on the upper side;
    wherein the gel coat of the gel pad positioned between the top surface of the operating table and the surgical underlay pad, adheres to both the top surface (30a) of the operating table (30) and to the underside of the surgical underlay pad so as to be sandwiched between the top surface (30a) and the underside and adhered thereto;
    wherein the shear strength of the gel coat is of a sufficient strength to prevent the gel pad from sliding across the top surface of the operating table and to prevent the surgical underlay pad from sliding across the surface of the gel pad.

11. The gel pad in claim 10, wherein the substrate is at least one of a polyurethane foam, a paper material, and a fabric.

12. The gel pad in claim 10, wherein the gel coat on the lower side of the substrate has a predetermined shear strength different than the predetermined shear strength of the gel coat on the upper side of the substrate.

13. A gel pad (100) for use with a surgical underlay pad configured to support a torso (40) of a patient lying on a top surface (30a) of an operating table (30) tilted beyond a horizontal plane, the gel pad comprising:
    a flexible substrate (10) having an upper side (10a) and a lower side (10b);
    a gel coat (20) comprising a polyurethane gel material on at least a portion of each of the lower side (10b) and the upper side (10a) of the substrate (10); and
    a sheet configured to support the torso;
    wherein at least one gel pad is configured to be positioned between the sheet and the torso;
    wherein the gel coat of the gel pad positioned between the top surface of the operating table and the surgical underlay pad, adheres to both the top surface (30a) of the operating table (30) and to the underside of the surgical underlay pad so as to be sandwiched between the top surface (30a) and the underside and adhered thereto; and
    wherein the shear strength of the gel coat is of a sufficient strength to prevent the gel pad from sliding across the top surface of the operating table and to prevent the surgical underlay pad from sliding across the surface of the gel pad.

* * * * *